United States Patent
Nakanishi et al.

(10) Patent No.: US 7,951,903 B2
(45) Date of Patent: May 31, 2011

(54) HYDRAZONE COMPOUND, HYDRAZONE COMPOUND FOR FORMING COMPLEX, LIGAND FOR FORMING METAL COMPLEX, AND MONOMER FOR MANUFACTURING POLYMER COMPOUND

(75) Inventors: Haruyuki Nakanishi, Susono (JP); Shinichi Matsumoto, Fuji (JP); Hidekazu Arikawa, Susono (JP); Hironobu Kumagai, Fuji (JP)

(73) Assignees: Toyota Jidosha Kabushiki Kaisha, Toyota-shi (JP); Ihara Chemical Industry Co., Ltd., Taito-ku (JP)

( * ) Notice: Subject to any disclaimer, the term of this patent is extended or adjusted under 35 U.S.C. 154(b) by 0 days.

(21) Appl. No.: 12/201,469

(22) Filed: Aug. 29, 2008

(65) Prior Publication Data
US 2009/0062507 A1    Mar. 5, 2009

(30) Foreign Application Priority Data

Aug. 31, 2007  (JP) .................................. 2007-225268

(51) Int. Cl.
    *C08G 73/06*    (2006.01)
(52) U.S. Cl. ................ 528/423; 564/227; 546/2
(58) Field of Classification Search ............ 528/149, 528/423, 210; 546/2
    See application file for complete search history.

(56) References Cited

U.S. PATENT DOCUMENTS
2004/0053977 A1 *  3/2004  Almstead et al. ............ 514/357

FOREIGN PATENT DOCUMENTS

| WO | 2004-036674 A2 | 4/2004 |
| WO | 2006-005724 A2 | 1/2006 |
| WO | 2006-008319 A2 | 1/2006 |
| WO | 2006-045673 A1 | 5/2006 |
| WO | 2006-063992 A2 | 6/2006 |
| WO | 2006-074829 A1 | 7/2006 |

* cited by examiner

*Primary Examiner* — Randy Gulakowski
*Assistant Examiner* — Shane Fang
(74) *Attorney, Agent, or Firm* — Kenyon & Kenyon LLP

(57) ABSTRACT

A hydrazone compound represented by a General Formula (1) below, a hydrazone compound for forming a metal complex, which is represented by the General Formula (1) below and forms a metal complex by coordination to at least one metal species, a ligand for forming a metal complex including the hydrazone compound, and a monomer for manufacturing a polymer compound including the hydrazone compound:

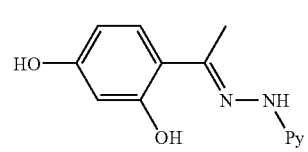

Formula (1)

wherein, Py represents a 2-pyridyl group, a 3-pyridyl group, or a 4-pyridyl group.

3 Claims, 4 Drawing Sheets

HYDRAZONE COMPOUND, HYDRAZONE COMPOUND FOR FORMING COMPLEX, LIGAND FOR FORMING METAL COMPLEX, AND MONOMER FOR MANUFACTURING POLYMER COMPOUND

INCORPORATION BY REFERENCE

The disclosure of Japanese Patent Application No. 2007-225268 filed on Aug. 31, 2007 including the specification, drawings and abstract is incorporated herein by reference in its entirety.

BACKGROUND OF THE INVENTION

1. Field of the Invention

The present invention relates to a novel hydrazone compound suitable as a starting material for a synthetic polymer or a starting material for a metal catalyst support.

2. Description of the Related Art

For example, platinum, cobalt, nickel, iron and alloys such as platinum-ruthenium alloys are known as electrode catalysts for fuel cells. It is important to increase catalytic action of these catalytic metals in order to increase the power generation capacity of fuel cells. For example, a catalyst utilization ratio is increased by finely powdering the catalytic metal. However, fine particles are very easily aggregated, the dispersed state thereof is difficult to maintain over a long period, and the catalyst utilization ratio cannot be sufficiently increased. Accordingly, fine particles of catalytic metals are supported on electrically conductive particles such as carbon particles and metal particles with the object of realizing fine dispersion of the catalytic metals, but the effect produced is insufficient. Further, methods for manufacturing the conventional electrode catalysts and electrodes having electrode catalysts dispersed therein require complex operations and processes, and there is a need for the development of a starting material compound for an electrode catalyst that can be manufactured by simpler operations and processes.

On the other hand, it is known that a catalyst for fuel cells can be manufactured by coordinating a metal to a synthetic polymer manufactured by using a certain hydrazone compound as a starting material to obtain a complex and then calcining the synthesized polymer metal complex (International Patent Application WO2004/036674).

SUMMARY OF THE INVENTION

With the foregoing in view, the inventors have conducted a comprehensive research of various novel hydrazone compounds and have found that a novel hydrazone compound represented by a specific general formula is suitable as a starting material compound for an electrode catalyst. Thus, the present invention provides a hydrazone compound useful as a starting material compound for an electrode catalyst that enables fine dispersion of a catalytic metal.

A hydrazone compound according to an aspect of the present invention is a novel compound represented by a General Formula (1) below:

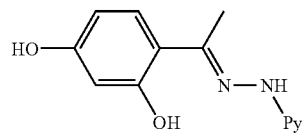

Formula (1)

wherein, Py represents a 2-pyridyl group, a 3-pyridyl group, or a 4-pyridyl group.

The hydrazone compound according to the aspect of the present invention that is represented by Formula (1) above has a coordination capacity due to hydrazone nitrogen (=N—) of a hydrazone group (=NNH$_2$), a hydroxyl group of a phenol and/or nitrogen (pyridine nitrogen) of a pyridine ring, and can form a stable complex due to the molecular structure thereof. Therefore, by coordinating the hydrazone compound according to the aspect of the present invention to a catalytic metal species, it is possible to disperse finely the catalytic metal in a stable state. Further, the hydrazone compound according to the aspect of the present invention can be polymerized with another compound in the presence of an acidic or basic catalyst to form a polymer compound. Moreover, after coordinating to a metal species (central metal ion, metal atom) and completing, it is also possible to covert the hydrazone metal complex into a polymer. As described above, the hydrazone compound according to the aspect of the present invention is very reactive and extremely useful as a starting material compound for complexes, polymer materials, and other compounds, and can be used as a ligand for forming metal complexes and a monomer for manufacturing polymer compounds. Among these applications, the hydrazone compound is exceptionally suitable for forming a metal complex as a ligand that forms a metal complex by coordination to at least one metal species.

According to the aspect of the present invention, it is possible to provide a hydrazone compound useful as a starting material compound for an electrode catalyst that enables fine dispersion of a catalytic metal and as a starting material compound for synthetic polymers.

BRIEF DESCRIPTION OF THE DRAWINGS

The foregoing and further features and advantages of the invention will become apparent from the following description of example embodiments with reference to the accompanying drawings, wherein like numerals are used to represent like elements and wherein.

DETAILED DESCRIPTION OF EMBODIMENTS

Figure 1:
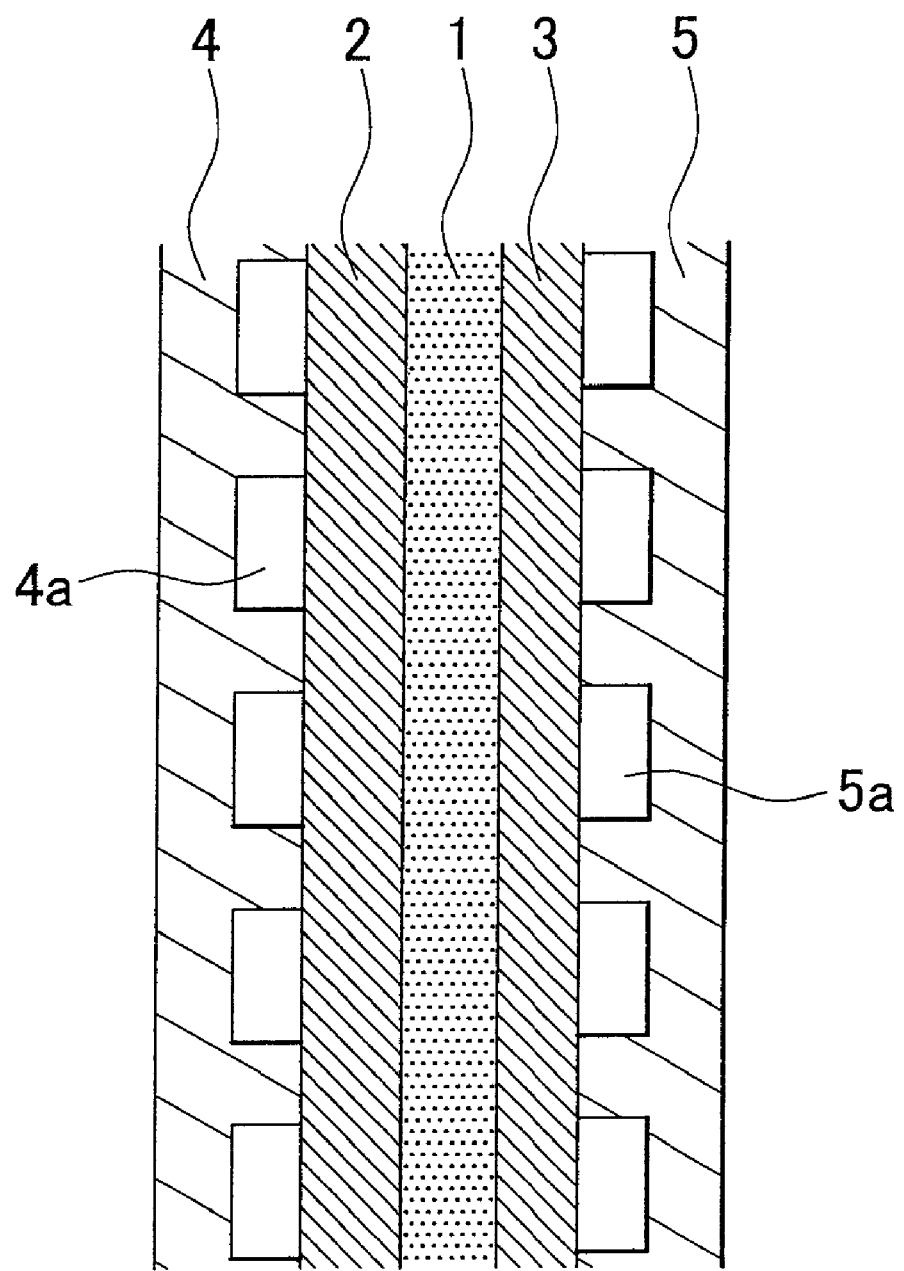
FIG. 1 is a cross-sectional view illustrating schematically a cell for an alkali fuel cell.

The novel hydrazone compound provided by the present invention is represented by General Formula (1) below:

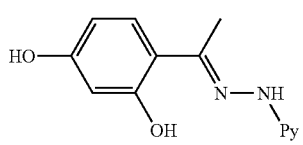

Formula (1)

wherein, Py represents a 2-pyridyl group, a 3-pyridyl group, or a 4-pyridyl group.

In the hydrazone compound in accordance with the present invention, the group represented by Py may be any group selected from among a 2-pyridyl group, a 3-pyridyl group, and a 4-pyridyl group, but from the standpoint of ability to form tridentate coordination in a molecule, the 2-pyridyl group is preferred. Further, there are E (Entgegen) isomers and Z (Zusammen) isomers of the hydrazone compound provided by the present invention, and the hydrazone compound can be obtained as a pure E isomer, a pure Z isomer, or a mixture containing the two isomers at a random ratio, but it is typically represented by General Formula (1). Specific examples of hydrazone compounds represented by General Formula (1) include 4-{1-[(2-pyridine-2-yl)hydrazono]ethyl}benzene-1,3-diol, 4-{1-[(3-pyridine-2-yl)hydrazono]ethyl}benzene-1,3-diol, and 4-{1-[(4-pyridine-2-yl)hydrazono]ethyl}benzene-1,3-diol.

In the hydrazone compound in accordance with the present invention that is represented by General Formula (1) above, hydrazone nitrogen, pyridine nitrogen, and/or a hydroxyl group of the phenol has coordination ability and can function as a ligand to form a complex. Moreover, the complex obtained by the coordination of the hydrazone compound in accordance with the present invention has excellent stability. The stability of the complex obtained is apparently derived from the structure of the coordination site of the hydrazone compound in accordance with the present invention. Thus, nitrogen (=N—) of the hydrazono group that is a coordination site of the hydrazone compound forms a C-shaped structure together with carbon adjacent to this nitrogen, carbon in a 4 position and a 3 position of a phenol to which the hydrazono group is bound, and oxygen (hydroxyl group) bound to a 3 position of a benzene ring of the phenol, and coordination bonds are formed by the hydrazone nitrogen (=N—) and the metal and also by the hydroxyl group of the phenol and the metal. As a result, it can be supposed that a hexagonal structure is formed by the central metal species and the hydrazone nitrogen (=N—), carbon adjacent to the hydrazone nitrogen, carbon in a 4 position and a 3 position of the phenol to which the hydrazono group is bound, and oxygen bound to a 3 position of the benzene ring of the phenol that form the C-shaped structure, and this hexagonal structure ensures excellent stability (see Formula (4) below)

Formula (4)

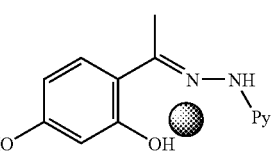

: Metal species

Further, in the hydrazone compound represented by Formula (1) above, nitrogen (pyridine nitrogen) of a pyridine ring that is bound to the hydrazono group also has coordination ability and supposedly contributes to the formation of the metal complex. Regarding this coordination, when the pyridine nitrogen is in a 3 position or 4 position of the pyridine ring, the metal complex is supposedly formed by a contribution of a plurality of hydrazone compound molecules. On the other hand, when the nitrogen is in a 2 position of the pyridine ring, the metal complex is supposedly formed by the formation of the so called tridentate coordination in the molecule.

The formation of the complex inhibits the aggregation of metal species and increases the dispersivity thereof. As described above, because the complex in which the hydrazone compound in accordance with the present invention above serves as a ligand has high stability, the dispersivity of metal species can be further increased. Moreover, this dispersivity can be maintained over a long period. For this reason, by using the hydrazone compound in accordance with the present invention as a ligand (ligand for forming a metal complex), coordinating it to a catalytic metal species, and forming a complex, it is possible to ensure fine dispersion of the catalytic metal. As a result, the utilization ratio of the catalytic metal species can be increased. Therefore, in accordance with the present invention, the growth of grains occurring in the manufacturing process or utilization of fine particles of catalytic metals is inhibited and a catalyst demonstrating excellent catalytic action with a small amount of catalytic metal can be obtained. Further, by employing the metal complex obtained by using the hydrazone compound in accordance with the present invention and a catalytic metal as a starting material compound for an electrode catalyst, it is also possible to obtain a fuel cell with excellent power generation capacity. In addition, the metal complex in which the hydrazone compound in accordance with the present invention and the catalytic metal are coordination bound can be manufactured by the typical conventional method and can be obtained by very simple operations and processes with excellent productivity.

The hydrazone compound represented by Formula (1) above can be also used as a starting material for a synthetic polymer compound, that is, as a monomer for manufacturing a polymer compound, and a hydrazone polymer compound can be obtained by polymerizing this starting material with other compounds, or a hydrazone polymer metal complex can be formed by further coordinating to a metal species to form a hydrazone metal complex and then using the hydrazone metal complex as a monomer. In the hydrazone polymer metal complex thus obtained by coordinating a hydrazone polymer compound containing a structural unit derived from the hydrazone compound to a catalytic metal or by polymerizing the hydrazone metal complex with another monomer, it is possible to improve further the dispersivity of the catalytic metal with respect to that of the hydrazone compound metal complex (monomer).

As described above, the hydrazone compound in accordance with the present invention is very useful as a starting material compound for complexes, polymer materials, and other compounds and can be used as a ligand for forming a metal complex or as a monomer for manufacturing a polymer compound. In addition, this hydrazone compound can be expected to find use and application in a variety of field. Among them, from the standpoint of ligand stability in complex formation, the hydrazone compound is very suitable as a hydrazone compound for forming a metal complex by coordination to at least one metal species, and the hydrazone compound can demonstrate excellent performance as a support for finely dispersing the metal species.

A method for manufacturing the hydrazone compound in accordance with the present invention is not particularly limited, and the hydrazone compound can be manufactured, for example, according to the reaction scheme shown below.

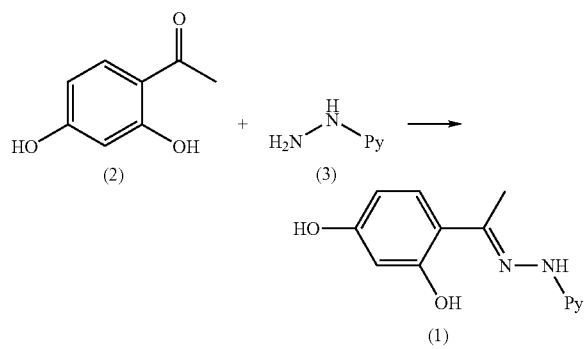

wherein, Py represents a 2-pyridyl group, a 3-pyridyl group, or a 4-pyridyl group The hydrazone compound in accordance with the present invention that is represented by General Formula (1) can be manufactured by reacting a ketone compound (2,4-dihydroxyacetophenone) represented by General Formula (2) and a hydrazine compound (hydrazinopyridine) represented by General Formula (3) in an appropriate solvent or without a solvent in the presence of a condensation agent or without such. The ketone compound represented by General Formula (2) and the hydrazine compound represented by General Formula (3) are well-known compounds and can be purchased as commercial products or synthesized by typical methods. As for the amount of each compound used in the reaction, the amount of the hydrazine compound represented by General Formula (3) is usually within a range of 0.8 to 10 mol, preferably 1.0 to 5.0 mol, more preferably 1.0 to 2.0 mol with respect to 1 mol of the ketone compound represented by General Formula (2).

The reaction proceeds in the presence of an acid catalyst, but it is preferred that a condensation agent be used to accelerate the reaction. Specific examples of acid catalysts include protonic acids such as hydrochloric acid, concentrated sulfuric acid, phosphoric acid, and acetic acid. Specific examples of condensation agents include typically used condensation agents such as DCC (dicyclohexylcarbodiimide). As for the amounts of the acid catalyst and condensation agent used, usually the acid catalyst and condensation agent are each used in an amount within a range of 0.0001 to 10 mol, preferably 0.0001 to 5 mol, more preferably 0.0001 to 2 mol with respect to 1 mol of the ketone compound represented by General Formula (2).

The aforementioned reaction also proceeds without a solvent, but a solvent is preferably used so that the reaction can proceed more smoothly. Any stable solvent that does not hinder the reaction can be used. Examples of suitable solvents include ethers such as phenyl ether and anisol, aromatic hydrocarbons such as toluene, xylene, mesitylene, and tetraline, alicyclic hydrocarbons such as decaline, aprotic polar solvents such as N,N-dimethylformamide (DMF), N,N-dimethylacetamide (DMAC), N,N-dimethylimidazolidinone (DMI), N-methylpyrrolidone (NMP), dimethylsulfoxide (DMSO), and sulfolan (TMSO$_2$), aromatic nitro compounds such as nitrobenzene and p-nitrotoluene, and aromatic halogenides such as chlorobenzene, o-dichlorobenzene and trichlorobenzene. The amount of solvent used is usually within a range of 0 to 3.0 L, preferably 0.05 to 1.5 L with respect to 1 mol of the ketone compound represented by General Formula (3).

The reaction temperature is not particularly limited, provided that the reaction proceeds. Usually, the reaction temperature is within a range of −20° C. to 150° C., preferably 10° C. to 120° C., and more preferably 20 to 100° C. The reaction time is not particularly limited, but from the standpoint of inhibiting the formation of byproducts, it is preferred that the reaction time be 0.5 to 40 h. After the reaction, the precipitated crystals are separated by filtration or the like, washed, if necessary with an organic solvent such as methanol, water, and mixtures thereof, and dried. The drying temperature is not particularly limited, and the drying may be performed at any temperature provided that it is lower than the melting point or decomposition point of the hydrazone compound in accordance with the present invention. The drying is usually performed at a temperature within a range of 20 to 200° C., preferably 30 to 180° C., and more preferably 40 to 150° C.

As described hereinabove, the hydrazone compound in accordance with the present invention forms a complex by coordination bonding to a catalytic metal species (metal atom, metal ion) (see Formula (4) above). A metal species for coordination is not particularly limited and can be a transition metal, more specifically a transition metal of Groups 8 to 10 (Group VIIIA). Specific examples of suitable metals include iron, cobalt, nickel, ruthenium, rhodium, palladium, osmium, iridium, and platinum. Among them, iron, cobalt, and nickel can be advantageously used. The hydrazone metal complex obtained by coordinating the hydrazone compound in accordance with the present invention to a metal species can be enabled to demonstrate catalytic activity with respect to a specific chemical reaction by selecting a metal species for coordination and, if necessary, reducing the metal species (for example, an application as a catalyst for olefin polymerization can be considered).

A method for obtaining a hydrazone metal complex in which the hydrazone compound in accordance with the present invention is coordinated to a metal species is not particularly limited and can conform to a generally used procedure. For example, a hydrazone metal complex can be obtained by dispersing a hydrazone compound in a polar solvent that demonstrates low dissolving ability with respect to the hydrazone compound and the metal complex produced, more specifically, an appropriate solvent such as a ketone represented by acetone and an alcohol represented by methanol and ethanol, or a mixed solvent thereof, adding a metal salt serving as a source material for a catalytic metal species, mixing, adding a pH adjusting agent, and further mixing. Examples of other suitable solvents include alkylnitrile, chloroform, dichloromethane, and ethyl acetate. It is usually preferred that the hydrazone metal complex be manufactured within a temperature range of 20 to 60° C. The obtained hydrazone metal complex is separated by filtration or the like and, if necessary, isolated by washing with a polar solvent demonstrating low dissolving ability with respect to the metal complex formed, more specifically with an appropriate solvent such as water, a ketone represented by acetone, and an alcohol represented by methanol and ethanol and drying.

Examples of suitable metal salts include acetates, chlorides, sulfates, nitrates, sulfonates, and phosphates. These metal salts may be used individually or in combinations of a plurality thereof, according to the application. When a plurality of metal salts are used, it is possible to obtain a mixture of hydrazone metal complexes coordinated to each metal species at a ratio reflecting the loading ratio of the metal salts (calculated as metal atoms). Further, typical bases and acids including organic acid salts, organic acids, inorganic acid salts, and inorganic acids may be used as pH adjusting agents.

Specific examples include organic bases including tertiary amines such as triethylamine and pyridines, organic acids including sulfonic acids such as methanesulfonic acid and p-toluenesulfonic acid and carboxylic acids such as acetic acid; inorganic bases, for example, metal hydroxides such as sodium hydroxide and potassium hydroxide, metal carbonates such as sodium carbonate and potassium carbonate, and metal hydrogencarbonates such as sodium hydrogencarbonate and potassium hydrogencarbonate; and inorganic acids including hydrohalogenic acids such as hydrochloric acid, sulfuric acid, phosphoric acid, and nitric acid, specific examples including NaOH, KOH, $Na_2CO_3$, $NaHCO_3$, HCl, $H_2SO_4$, $HNO_3$, $KHSO_4$, and $CH_3COOH$.

A hydrazone polymer compound containing a structural unit derived from the hydrazone compound can be obtained by polymerizing the hydrazone compound in accordance with the present invention with another compound. More specifically, for example, a hydrazone polymer compound can be obtained by polymerizing at least the hydrazone compound, a phenol, and an aldehyde. Even more specifically, a hydrazone polymer compound represented by Formula (5) below can be obtained by polymerizing the hydrazone compound in accordance with the present invention, phenol, and formaldehyde in the presence of a base or an acid catalyst.

Formula (5)

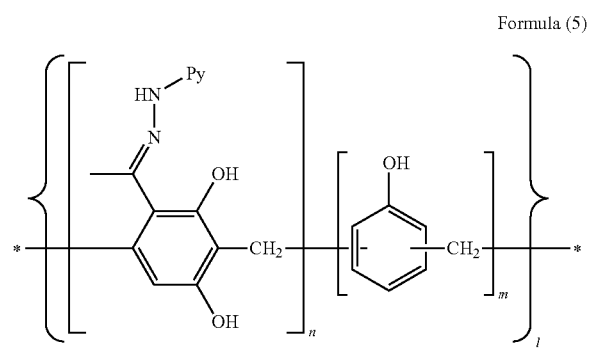

In Formula (5) above, n, m are each integer equal to or larger than 1. Further, l is integer equal to or larger than 2. Examples of suitable phenols include phenol and compounds obtained by bonding one, or two or more substituents to phenol. Examples of substituents that can be introduced into phenol include —OH, —OR, —NR'R", and an aryl group or alkyl group having 1 to 15 carbon atoms (may have a branched structure). In this case, because high polymerization ability can be expected, it is preferred that the compound has electron donating ability. R is not particularly limited, provided it is an alkyl substituent or aryl substituent, but an alkyl group or aryl group having 1 to 10 carbon atoms is preferred. Further, R' and R" are not particularly limited, provided that they are monovalent organic groups, each preferably being, independently from each other, hydrogen, or an alkyl group having 1 to 10 carbon atoms, or an aryl group.

Examples of preferred aldehydes include formaldehyde, and paraformaldehyde.

A specific method for manufacturing the hydrazone polymer compound represented by Formula (5) above includes dissolving or dispersing the hydrazone compound in accordance with the present invention, a phenol, and an aldehyde in an appropriate solvent (for example, an appropriate solvent such as water, ketones represented by acetone, and alcohols represented by methanol and ethanol, or mixtures thereof), and inducing condensation of the hydrazone compound and the aldehyde, and he phenol and the aldehyde by setting predetermined temperature conditions (for example, 20° C. to 150° C.) in the presence of a base such as NaOH or an acid such as HCl.

In the hydrazone polymer compound represented by Formula (5) above, a ratio of structural units derived from the hydrazone compound and structural units derived from a phenol is not particularly limited and can be appropriately selected.

The hydrazone compound in accordance with the present invention is not limited to the hydrazone polymer compound of the above-described structure, and a polymer of higher molecular weight can be obtained by polymerization with another compound. More specifically, a coordination polymer of a higher molecular weight can be obtained by performing heating and stirring under oxidation conditions of a resol resin synthesized in the presence of a base catalyst, or by adding a crosslinking agent such as hexamethylenetetramine to a novolak resin synthesized under acidic conditions.

Similarly to the hydrazone compound, a hydrazone polymer compound obtained by using the hydrazone compound as a monomer can form a hydrazone polymer metal complex by coordination with a metal species in hydrazone nitrogen originating in the hydrazone compound, pyridine nitrogen, and/or a hydroxyl group of a phenol (see Formula (6) below). A method for coordinating the hydrazone polymer compound to a metal species is similar to the method for manufacturing a hydrazone metal complex from the hydrazone compound. When a plurality of metal salts are used for the hydrazone polymer compound, a hydrazone polymer metal complex can be obtained that contains the metal species at a ratio reflecting the loading ratio of the metal salts (calculated as metal atoms). Affinity for the metals generally differs depending on the synthesized polymer, and the content of metal can be controlled by the molecular structure by using this difference.

Formula (6)

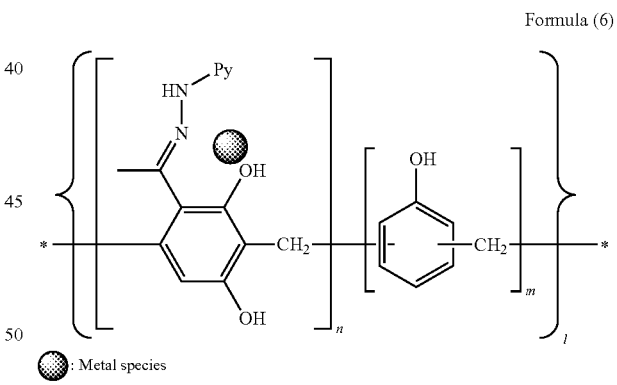

⬤ : Metal species

Alternatively, by polymerizing the above-described hydrazone metal complex with another compound, it is possible to obtain a hydrazone polymer metal complex containing structural units derived from the hydrazone metal complex. More specifically, a hydrazone polymer metal complex having a structure similar to that represented by Formula (6) above can be manufactured by polymerizing the hydrazone metal complex with a phenol and an aldehyde. The polymerization of the hydrazone metal complex, phenol, and aldehyde can be performed under the same conditions as those of the above-described polymerization reaction of the hydrazone compound, phenol, and aldehyde.

The above-described hydrazone metal complex and hydrazone polymer metal complex (can be together referred to hereinbelow as "metal complex") can demonstrate catalytic activity with respect to electrochemical reactions upon calcining. Furthermore, where these are calcined together with an electrically conductive support material, the demonstrated catalytic activity can be higher than that obtained by calcining the metal complex alone. More specifically, where a hydrazone metal complex or hydrazone polymer metal complex in which a hydrazone compound is coordinated to a metal catalyst species such as Pt, Ni, Fe, Co, Ag, Pd, Cu, Mn, Mo, Ru, Rh, and Cr is calcined together with a carbonaceous electrically conductive support material such as active carbon, partial bonds are formed between the hydrazone and carbonaceous electrically conductive support material, and the hydrazone metal complex or hydrazone polymer metal complex is immobilized on the surface of the carbonaceous electrically conductive support material. The hydrazone metal complex—carbonaceous electrically conductive support material composite or hydrazone polymer metal complex—carbonaceous electrically conductive support material composite that are thus produced can function as electrically conductive supports for catalytic metals, and the catalytic metals supported on such composites can demonstrate catalytic activity with respect to electrochemical reactions.

The calcination of the metal complex is preferably performed under inactive gas atmosphere or reducing conditions such as hydrogen gas atmosphere. By performing the calcination under inert atmosphere or reducing conditions, it is possible to impart catalytic activity with respect to electrochemical reaction, without oxidizing the hydrazone compound or hydrazone polymer compound coordinated to a catalytic metal and to maintain the coordination structure of the catalytic metal and hydrazone compound or hydrazone polymer compound. Calcination conditions such as calcination temperature and calcination time may be appropriately determined with consideration for types of the hydrazone compound or hydrazone polymer compound and metal catalyst constituting the metal complex and application of the catalyst. However, it is important that the calcination temperature and calcination time be set such that catalytic activity with respect to electrochemical reactions be imparted and the structure of coordination sites of the catalytic metal and nitrogen derived from the hydrazone compound or hydrazone polymer compound be retained even after the calcination. Where the calcination temperature is too high or the calcination time is too long, the coordination state of catalytic metal cannot be maintained, the metal catalyst is not supported on the calcined body of the hydrazone compound or calcined body of the hydrazone copolymer compound, and the finely dispersed state of catalytic metal is difficult to maintain.

The advantage of calcining the hydrazone metal complex and hydrazone polymer metal complex in the presence of an electrically conductive support material that can support the catalyst obtained by the calcination is that in addition to the above-described high catalytic activity, it is possible to support on the electrically conductive support material the catalyst that is obtained simultaneously with catalyzation of these metal complexes. By supporting the catalyst obtained by calcining the hydrazone metal complex or hydrazone polymer metal complex on an electrically conductive support material, it is possible to realize even finer dispersion of the metal catalyst. Examples of suitable electrically conductive support materials include electrically conductive materials that have been generally used as supports for supporting catalytic metals, for example, carbon particles such as active carbon (more specifically, Vulcan XC-72R, Ketchenblack etc.) and metal particles, e.g. porous oxides such as $Al_2O_3$, $SiO_2$, and $CeO_2$. These electrically conductive materials may be molded into sheets. According to the catalyst application, the hydrazone metal complex or hydrazone polymer metal complex may be subjected to reduction treatment to reduce the coordination metal prior to the calcination. A typical method of reduction treatment can be used. For example, a method can be employed that uses a reducing agent such as hydrogen gas, alkali metal borohydrides, quaternary ammonium borohydrides, diboranes, hydrazine, alcohols, and amino alcohols.

As for specific calcination conditions, for example, in order to obtain an anode catalyst of a fuel cell (catalyst for fuel oxidation reaction), first, precalcining is performed for 1 to 10 h at 250 to 450° C. in hydrogen gas atmosphere or in the presence of a chemical reducing agent such as $NaBH_4$, $KBH_4$, $LiBH_4$, a tetrahydroborate salt ($XBH_4$) using tetraalkylammonium ($NR_4^+$) or the like as a cation, and $NaH_2PO_2$, thereby reducing a metal species coordinated to the hydrazone compound or hydrazone polymer compound. Then, calcination is performed for 1 to 2 h at 350 to 400° C. under reducing conditions (more specifically under hydrogen gas atmosphere). In this case, as described hereinabove, by performing the calcination upon mixing with an electrically conductive support material, it is possible to support the catalyst obtained by the calcination on the electrically conductive support material and to produce a catalyst with a higher catalytic activity. On the other hand, in order to obtain a cathode catalyst for a fuel cell (reduction catalyst for an oxidizing agent), calcination is performed for 1 to 2 h at 500 to 1000° C., preferably 800° C. under inactive gas atmosphere such as nitrogen gas atmosphere or argon gas atmosphere. In this case, similarly to the anode catalyst, by performing the calcination upon mixing with an electrically conductive support material as described hereinabove, the catalyst obtained by the calcination can be supported on the electrically conductive support material and a catalyst with higher catalytic activity can be produced.

With the above-described catalyst obtained using the hydrazone compound in accordance with the present invention, when a rare metal such as platinum is used, the amount thereof can be decreased. Moreover, excellent catalytic action is produced even without using a rare metal such as platinum. Accordingly, the catalyst in accordance with the present invention has a high industrial value. The catalyst can be used in a variety of fields such as an electrode catalyst of a fuel cell, a catalyst for exhaust gas purification in automobiles and the like, and an ammonium decomposition catalyst. Examples of fuel cells include alkali fuel cells in which charge carriers are hydroxyl ions ($OH^-$) and also solid polymer electrolyte fuel cells, solid oxide fuel cells, and phosphate fuel cells in which charge carriers are protons ($H^+$). By using the catalyst obtained by employing the hydrazone compound in accordance with the present invention, it is possible to manufacture easily an electrode with excellent dispersivity of a catalytic metal. Among possible applications, the preferred one is to alkali fuel cells in which charge carriers are hydroxyl ions and a base metal such as Ni, Fe, and Co can be advantageously used as an electrode catalyst. In applications as catalysts for alkali fuel cells, it is preferred to use hydrazone metal complexes or hydrazone polymer metal complexes in which Group 8 transition metals, Group 9 transition metals, Group 10 transition metals, and Group 11 transition metals serve as central metals. In particular, it is preferred to obtain multielement systems such as mixtures in which at least two or more, or three or more hydrazone metal complexes from among hydrazone metal complexes coordinated to Group 8 transition metals, hydrazone metal complexes coordinated to Group 9 transition metals, hydrazone metal complexes coordinated to Group 10 transition metals, and hydrazone metal complexes coordinated to Group 11 transition metals are combined, or hydrazone polymer metal complexes coordinated to two or more, or three or more transition metals selected from Group 8 transition metals, Group 9 transition metals, Group 10 transition metals, and Group 11 transition metals are combined.

More specifically, in the case of an anode catalyst of a direct ethanol fuel cell of an alkali type, Ni, Co, and Fe are preferred as the catalytic metal. In particular multicomponent systems using two or more of these catalytic metals, and among them three-component systems of Ni, Co, and Fe, are especially preferred. On the other hand, Ni, Co, Fe, and Mn are preferred as catalytic metals for a cathode catalyst of an alkali fuel cell. In particular, multicomponent systems using two or more of these catalytic metals, and among them two-component systems of Ni and Co are especially preferred.

An example of an alkali fuel cell will be explained below with reference to FIG. 1. However, alkali fuel cells are not limited to the below-described structure. The alkali fuel cell uses an aqueous solution of potassium hydroxide or an anion exchange resin as an electrolyte 1, and hydroxyl ions generated by a reaction of oxygen and water ($\frac{1}{2}O_2 + H_2O \rightarrow 2HO^-$) in an oxidizing agent electrode 3 move via the electrolyte 1 to a fuel electrode 2, where water and electrons are generated by a reaction with a fuel (hydrogen gas and the like) in the fuel electrode ($H_2 + 2OH^- \rightarrow 2H_2O + 2e^-$). Water generated in the fuel electrode 2 moves via the electrolyte 1 to the oxidizing agent electrode and serves as a starting material for electrode reaction at the oxidizing agent electrode 3. The anion exchange resin is not particularly limited, provided that the hydroxyl ions generated at the oxidizing agent electrode can be moved to the fuel electrode. For example, a solid polymer membrane containing an anion exchange resin having anion exchange groups such as quaternary ammonium groups and pyridinium groups can be used.

The fuel electrode includes an electrode catalyst demonstrating a catalytic action inducing the generation of water from the hydrogen and hydroxyl ions, and the oxidizing agent electrode includes an electrode catalyst demonstrating a catalytic action inducing the generation of hydroxyl ions from the oxygen and water. Each electrode can have a configuration in which the electrode catalysts are disposed on a porous conductive body that includes a structure capable of supplying the fuel and oxidizing agent to the electrode catalyst and has electron conductivity. Examples of suitable porous conductive bodies include conductive carbonaceous materials such as carbon paper and carbon sheet, and also metal meshes and cellular bodies of Ni, Ti, and the like. The electrodes may have no porous conductive body, provided that the electrode catalyst is fixed. A fuel electrode separator 4 that is non-permeable to fuel and has electric conductivity is disposed on the outside of the fuel electrode, and an oxidizing agent electrode separator 5 that is non-permeable to the oxidizing agent and has electric conductivity is disposed on the outside of the oxidizing agent, thereby constituting a unit cell for a fuel cell. The electric power is generated by supplying the fuel containing hydrogen or a hydrogen-generating compound to the fuel electrode via the fuel electrode separator and supplying the oxidizing agent containing air or an oxygen-generating compound to the oxidizing agent electrode via the oxidizing agent electrode separator.

EXAMPLES

Manufacture of Hydrazone Compound

A total of 33.8 g (0.309 mol) of 2-hydrazinopyridine and 2 L of methanol were charged into a four-neck flask with a capacity of 3 L equipped with a reflux condenser, a thermometer, and a stirrer, and 1 mL of concentrated sulfuric acid was then dropwise added at room temperature under stirring. Then, 44.0 g (0.289 mol) of 2,4-dihydroxyacetophenone was charged and a reaction was conducted for 8 h at 40° C. under stirring. The precipitated crystals were taken out by filtration, washed with methanol and water and dried at 60° C. to obtain 33.0 g of 4-{1-[(2-pyridine-2-yl)hydrazono]ethyl}benzene-1,3-diol in the form of light-yellow crystals. The yield was 50%. GC/MS, $^1$H-NMR, and IR measurements were performed with respect to the obtained crystals. The results are shown below.

Melting point: 230° C. GC/MS (EI): M/Z=243 (M$^+$) 228 (M$^+$—CH$_3$) $^1$H-NMR (300 MHz, DMSO-d$_6$): δ=2.33 (s, 3H), 6.26 (d, 1H, J=2.4 z), 6.31 (dd, 1H, J=2.4 Hz, J=8.7 Hz), 6.80 (ddd, 1H, J=0.7 Hz, J=5.1 Hz, J=7.2 Hz), 6.89 (d, 1H, J=8.4 Hz), 7.36 (d, 1H, J=8.7 Hz), 7.64 (ddd, 1H, J=1.8 Hz, J=7.2 Hz, J=8.4 Hz), 8.18 (ddd, 1H, J=0.7 Hz, J=1.8 Hz, J=5.1 Hz) δ=9.65 (s, 1H), δ=9.93 (s, 1H), δ=13.36 (s, 1H), IR (KBr, cm$^{-1}$): 3440, 3372, 1630, 1598, 1578, 1506, 1454, 1255, 767.

Manufacture of Hydrazone Polymer Compound

A total of 8 g of the hydrazone compound obtained in the above-described manner was suspended in 100 mL of an aqueous solution of ethanol (water:ethanol=1:2) in a 200 mL flask and a hydrazone solution was prepared. Then, 4.0 g of phenol, 4.0 mL of formaldehyde (37 wt %), and 0.25 g of NaOH were added to the hydrazone solution, reflux under heating was performed at 110° C., and the reaction was conducted for 6 h. After the reaction, the pH value was adjusted to 2 to 3 with an aqueous solution of HCl, and the reaction was further continued for 1 h. The suspension obtained was neutralized with an aqueous solution of NaOH, followed by filtration. The residue was washed three times with an aqueous solution of acetone [acetone:water=1:1]. The solid matter obtained (hydrazone polymer compound) was dried for 3 days at 65° C.

Manufacture of Hydrazone Metal Complex (1)

First, 0.5 g of the hydrazone compound obtained in the above-described manner was mixed and stirred with 100 mL of acetone. Then, 0.08 g of Co(AcO)$_2$.4H$_2$O, 0.13 g of Ni(AcO)$_2$.4H$_2$O, and 0.08 g of Fe(AcO)$_2$.4H$_2$O were added and the components were stirred. A total of 100 mL of a 1 M aqueous solution of NaOH was then added and the pH value was adjusted to about 9. The system was stirred for 10 h, followed by filtration. The residue was washed several times with water. The solid matter obtained (hydrazone metal complex (1)) was vacuum dried at 65° C.

Manufacture of Hydrazone Polymer Metal Complex (1)

First, 1.0 g of the hydrazone polymer compound obtained in the above-described manner was mixed and stirred with 20 mL of acetone. Then, 0.5 g of Co(AcO)$_2$.4H$_2$O, 0.5 g of Ni(AcO)$_2$.4H$_2$O, 0.5 g of Fe(AcO)$_2$.4H$_2$O, and 15 mL of acetone were added and the components were stirred. A total of 20 mL of a 1M aqueous solution of NaOH was then added and the pH value was adjusted to about 9. The system was stirred for 10 h, followed by filtration. The residue was washed several times with water. The solid matter obtained (hydrazone polymer metal complex (1)) was vacuum dried at 65° C.

Manufacture of Anode Catalyst (a)

Figure 2:
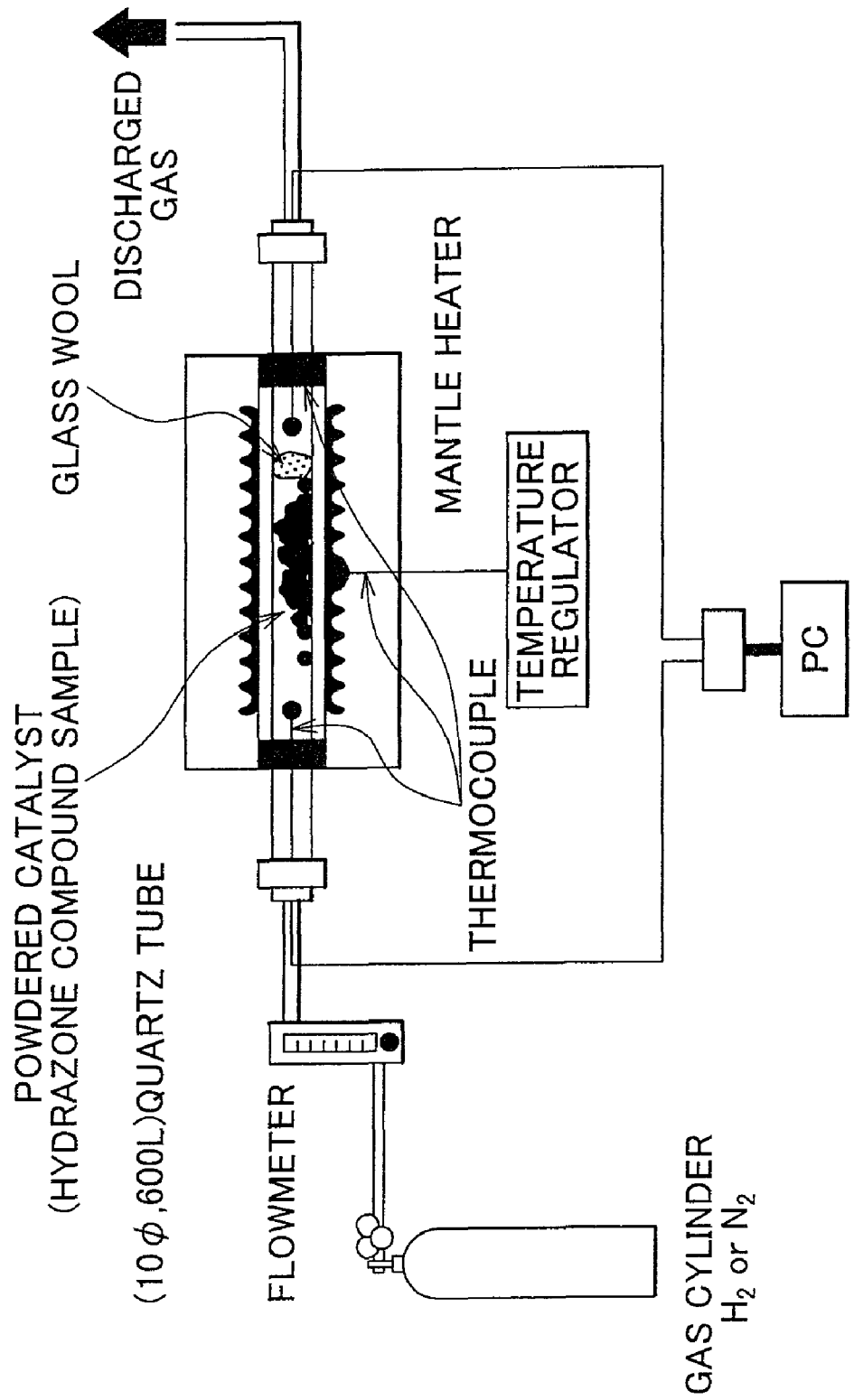
FIG. 2 is a schematic diagram of a heat treatment apparatus used in examples.

A total of 0.10 g of the hydrazone metal complex (1) obtained in the above-descried manner was mixed with 1.00 g of carbon particles (Vulcan XC-72R). The mixture was placed in a quartz glass tube, hydrogen gas was introduced into the quartz glass tube (250 mL/min), and the temperature was raised to 360° C. at a rate of 6.5° C. per minute (see a heat treatment apparatus shown in FIG. 2). The temperature of 360° C. was maintained for 2 h. An acetic acid salt of the hydrazone metal complex (1) was reduced and the metal complex was calcined. The temperature was then lowered to room temperature, the supply of hydrogen gas was stopped, and an anode catalyst (a) was obtained. In the heat treatment apparatus shown in FIG. 2, the temperature inside the quartz glass tube was monitored with a thermocouple and controlled with a temperature-adjustable mantle heater. The flow rate of gas introduced into the quartz glass tube was regulated with a flowmeter. Glass wool was used to prevent the sample located inside the tube from being moved by the gas flow.

Manufacture of Anode Catalyst (A)

A total of 0.10 g of the hydrazone polymer metal complex (1) obtained in the above-descried manner was mixed with 1.00 g of carbon particles (Vulcan XC-72R). The mixture was placed in a quartz glass tube, hydrogen gas was introduced into the quartz glass tube (250 mL/min), and the temperature was raised to 360° C. at a rate of 6.5° C. per minute (see FIG. 2). The temperature of 360° C. was maintained for 2 h. An acetic acid salt of the hydrazone polymer metal complex (1) was reduced and the polymer metal complex was calcined. The temperature was then lowered to room temperature, the supply of hydrogen gas was stopped, and an anode catalyst (A) was obtained.

Evaluation of Catalysts

Evaluation of Anode Catalyst (a)

Figure 3:
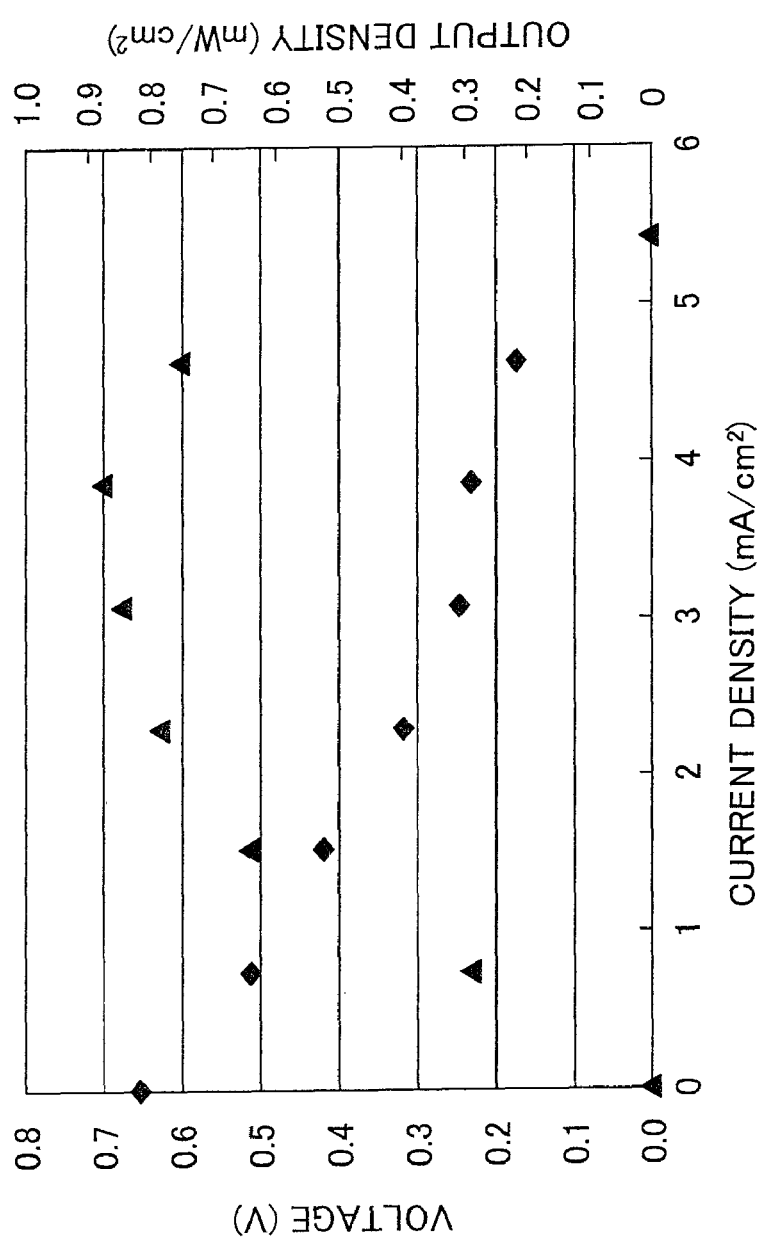
FIG. 3 is a graph illustrating the evaluation results of an anode catalyst (a) in examples.

A total of 0.5 g of the anode catalyst (a) obtained in the above-described manner was dispersed in about 10 mL of water, and the catalyst dispersion was coated (side 36 mm, thickness 0.3 mm) on a porous sheet (nickel foam, thickness about 1 mm) made of nickel. The coating was dried to obtain an anode electrode (thickness 0.3 mm). On the other hand, 0.5 g of the cathode catalyst (identical to the above-described anode catalyst (a)) was dispersed together with 0.05 g tetrafluoroethylene in about 10 mL of water by ultrasonic dispersion process, and the catalyst dispersion was spray coated (side 36 mm, thickness 0.2 mm) on a porous sheet (carbon sheet, thickness about 1 mm) made of carbon. The coating was dried to obtain a cathode electrode. An anion exchange membrane (hydrocarbon-based membrane, thickness 40 μm, side 65 mm) was sandwiched between the anode electrode and cathode electrode so as to be in contact with the surface of the anode electrode and cathode electrode coated with the catalyst dispersion, the laminate was disposed in a cell jig, and a fuel cell 1 for evaluation was produced. An I-V characteristic of the fuel cell 1 for evaluation was measured with a galvanostat under the following conditions. The results obtained are shown in FIG. 3.

<I-V Characteristic Measurement Conditions>

Anode fuel: KOH ethanol aqueous solution (ethanol, 10 wt %, KOH 1M), anode fuel flow rate: about 600 mL/min, cathode gas: air, cathode gas flow rate: 130 mL/min, temperature (thermostat temperature): 50° C.

Evaluation of Anode Catalyst (A)

Figure 4:
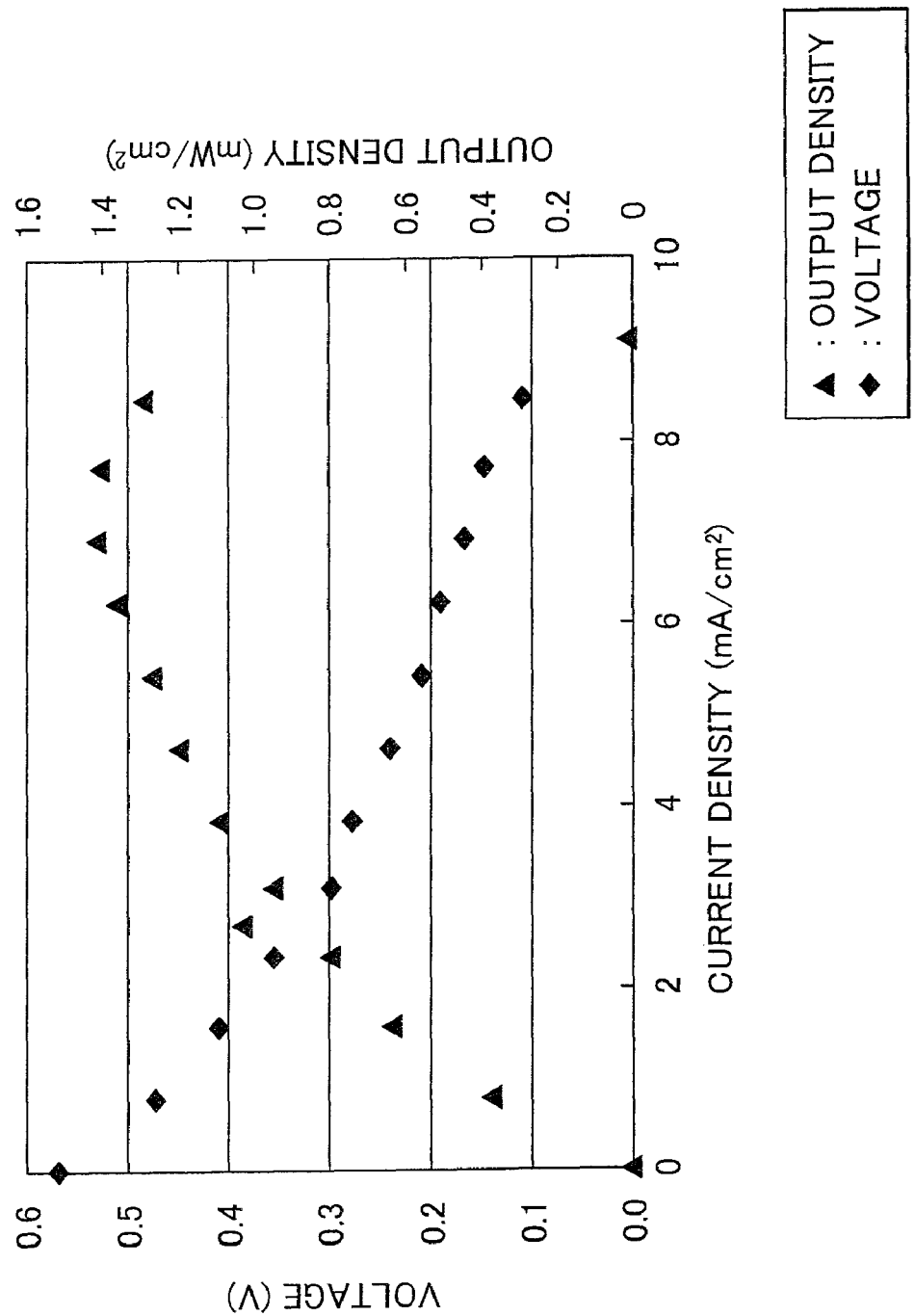
FIG. 4 is a graph illustrating the evaluation results of an anode catalyst (A) in examples.

A fuel cell 2 for evaluation was fabricated and the I-V characteristic was measured in the same manner as in the evaluation of the anode catalyst (a), except that the anode catalyst (A) was used instead of the anode catalyst (a) (for both the anode catalyst and the cathode catalyst). The results are shown in FIG. 4.

As shown in FIG. 3, the fuel cell 1 using the anode catalyst (a) in accordance with the present invention demonstrated good power generation performance, namely, an OCV of about 0.65 V and a maximum output density of about 0.88 mW/cm$^2$ (at a current density of 3.8 mA/cm$^2$). Further, as shown in FIG. 4, the fuel cell 2 using the anode catalyst (A) in accordance with the present invention demonstrated good power generation performance, namely, an OCV of about 0.58 V and a maximum output density of about 1.4 mW/cm$^2$ (at a current density of 6.4 mA/cm$^2$). These results indicate that the anode catalyst (A) obtained by calcining the hydrazone polymer metal complex makes it possible to obtain an output density substantially higher than that obtained with the anode catalyst (a) obtained by calcining the hydrazone metal complex. This is supposedly because the dispersivity of the catalytic metal in the electrode is higher when the hydrazone polymer metal complex is used than when the hydrazone metal complex is used.

What is claimed is:

1. A hydrazone metal complex, comprising:
a hydrazone compound represented by a General Formula (1) below:

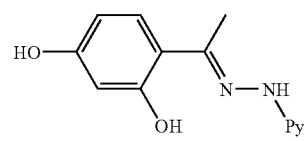

Formula (1)

wherein, Py represents a 2-pyridyl group, a 3-pyridyl group, or a 4-pyridyl group; and
at least one transition metal species coordinated to the hydrazone compound.

2. The hydrazone metal complex according to claim 1, wherein the transition metal specie is the transition metal of Groups 8 to 10.

3. The hydrazone metal complex according to claim 1, wherein the transition metal specie is at least one transition metal selected from iron, cobalt, nickel, ruthenium, rhodium, palladium, osmium, iridium and platinum.

* * * * *